United States Patent [19]
Ginn et al.

[11] Patent Number: 5,817,013
[45] Date of Patent: Oct. 6, 1998

[54] METHOD AND APPARATUS FOR THE MINIMALLY INVASIVE HARVESTING OF A SAPHENOUS VEIN AND THE LIKE

[75] Inventors: Richard Ginn, San Jose, Calif.; Mike Hooven; Ted Richardson, both of Cincinnati, Ohio

[73] Assignee: Enable Medical Corporation, Cincinnati, Ohio

[21] Appl. No.: 618,662

[22] Filed: Mar. 19, 1996

[51] Int. Cl.⁶ ..................................................... A61B 1/04
[52] U.S. Cl. .......................... 600/114; 600/101; 600/104
[58] Field of Search .................................... 600/101, 104, 600/106, 107, 108, 114, 153, 121, 123

[56] References Cited

U.S. PATENT DOCUMENTS

| | | | |
|---|---|---|---|
| 2,821,190 | 1/1958 | Chase | 600/114 X |
| 3,788,325 | 1/1974 | Jacobsen . | |
| 4,128,099 | 12/1978 | Bauer . | |
| 4,261,346 | 4/1981 | Wettermann . | |
| 4,493,321 | 1/1985 | Leather . | |
| 4,793,346 | 12/1988 | Mindich . | |
| 4,807,593 | 2/1989 | Ito | 600/114 |
| 4,821,718 | 4/1989 | Uldall . | |
| 5,025,778 | 6/1991 | Silverstein et al. | 600/104 |
| 5,258,006 | 11/1993 | Rydell et al. . | |
| 5,259,366 | 11/1993 | Reydel et al. | 600/104 X |
| 5,281,220 | 1/1994 | Blake, III . | |
| 5,320,636 | 6/1994 | Slater . | |
| 5,330,471 | 7/1994 | Eggers . | |
| 5,331,971 | 7/1994 | Bales et al. . | |
| 5,372,601 | 12/1994 | Lary . | |
| 5,373,840 | 12/1994 | Knighton . | |
| 5,392,789 | 2/1995 | Slater et al. . | |
| 5,478,351 | 12/1995 | Meade et al. . | |
| 5,645,519 | 7/1997 | Lee et al. | 600/114 |

OTHER PUBLICATIONS

"An Improved Technique for Long Saphenous Vein Harvesting for Coronary Revascularization", W. Meldrum–Hanna F.R.A.C.S.
*Thoracic and Cardiovascular Surgery*, vol. 42 Jul., 1986, pp. 90–92.

*Primary Examiner*—Beverly M. Flanagan
*Attorney, Agent, or Firm*—Lyon & Lyon LLP

[57] ABSTRACT

A minimally invasive technique for harvesting saphenous veins and the like for use as autografts in coronary artery bypass grafting surgery include a microsurgical instrument adapted to be demountably secured to the distal end of an endoscope. The instrument is inserted through an entry incision in the patient's skin, at the end of the endoscope which is used by a surgeon to advance the instrument along the saphenous vein, using the vein as a guide for the instrument. The instrument is tapered to provide initial separation of surrounding tissues from the vein, and cutting means supported by the instrument and viewed via the endoscope allow dissection of all tissues and side branch vessels from the saphenous vein. The instrument further provides a protective hood which prevents tissues or skin from blocking the endoscope. The desired length of saphenous vein is transected and is extracted via the entry incision. The technique minimizes trauma to the patient and to the saphenous vein graft.

4 Claims, 3 Drawing Sheets

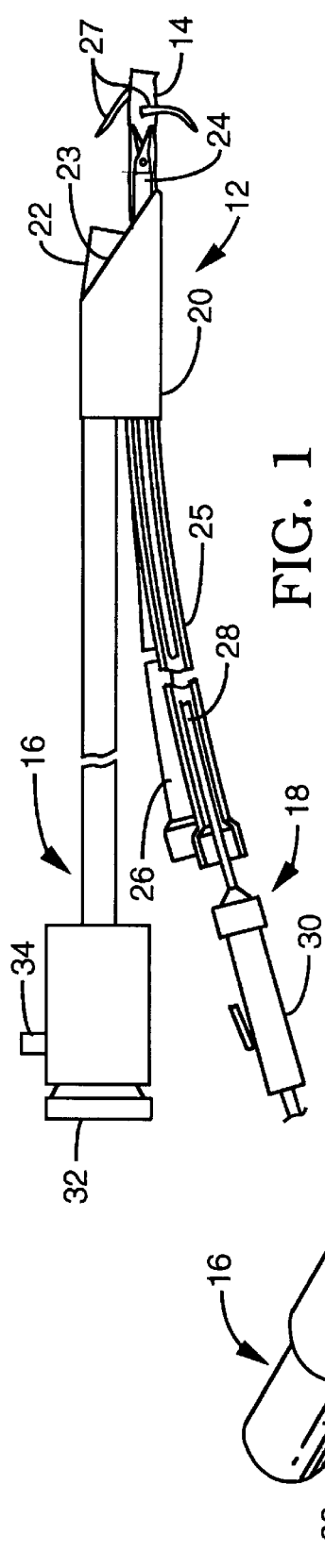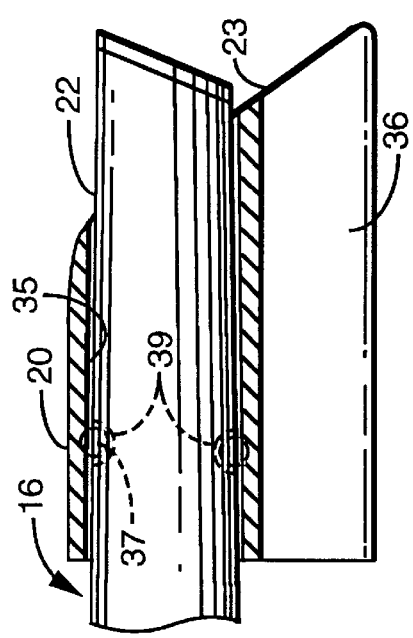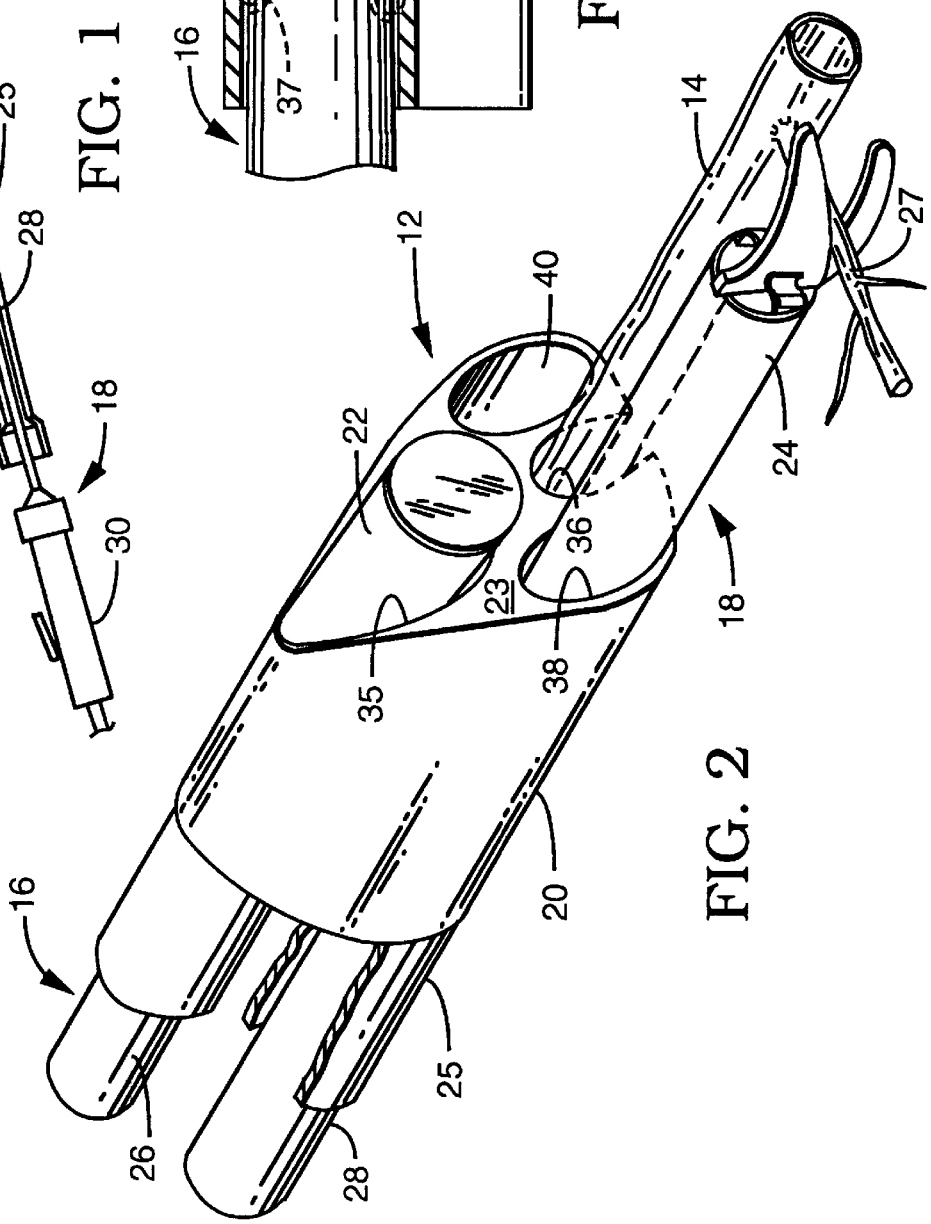

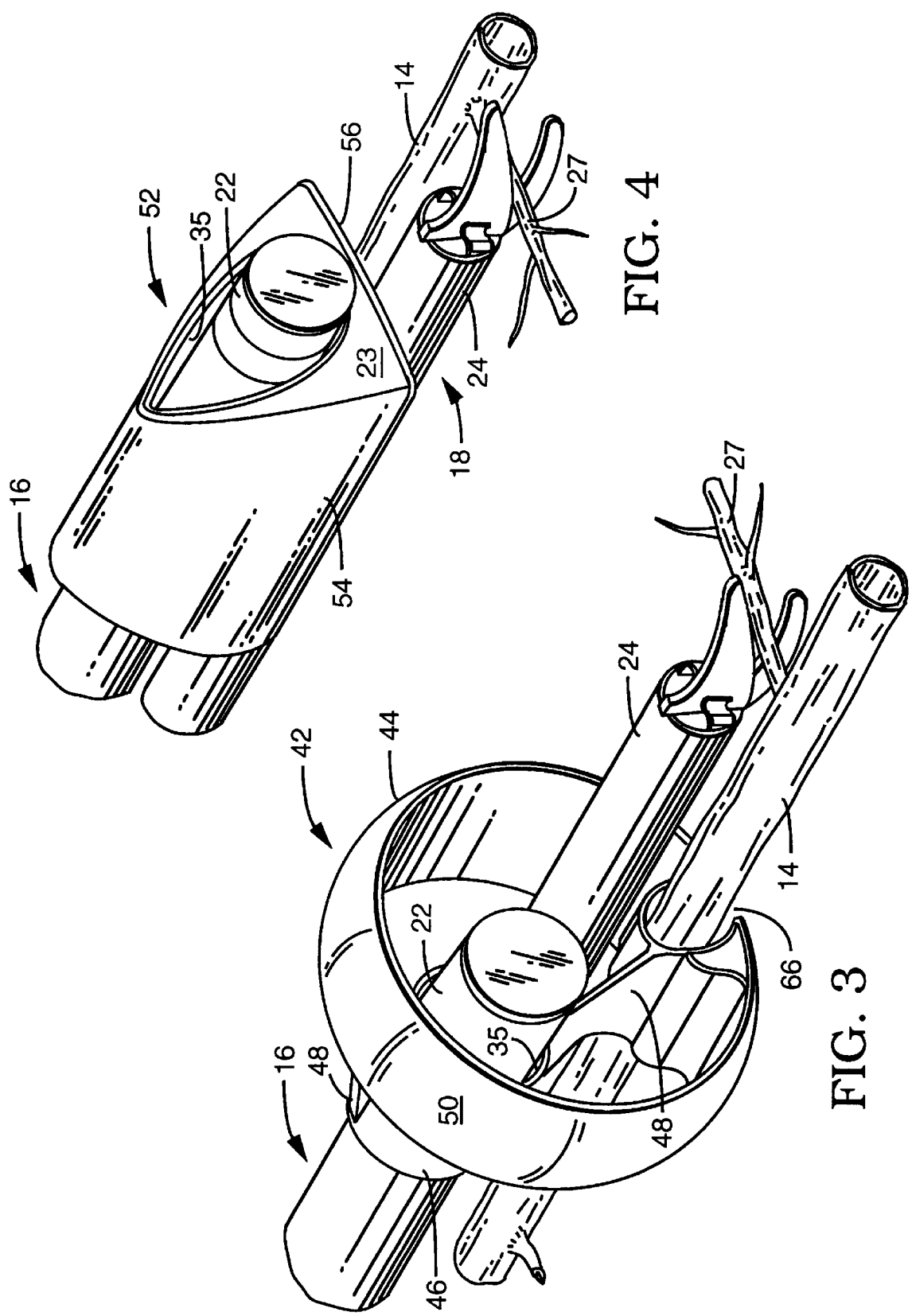

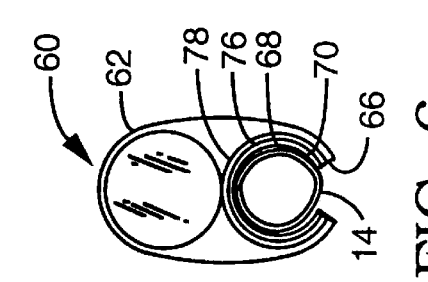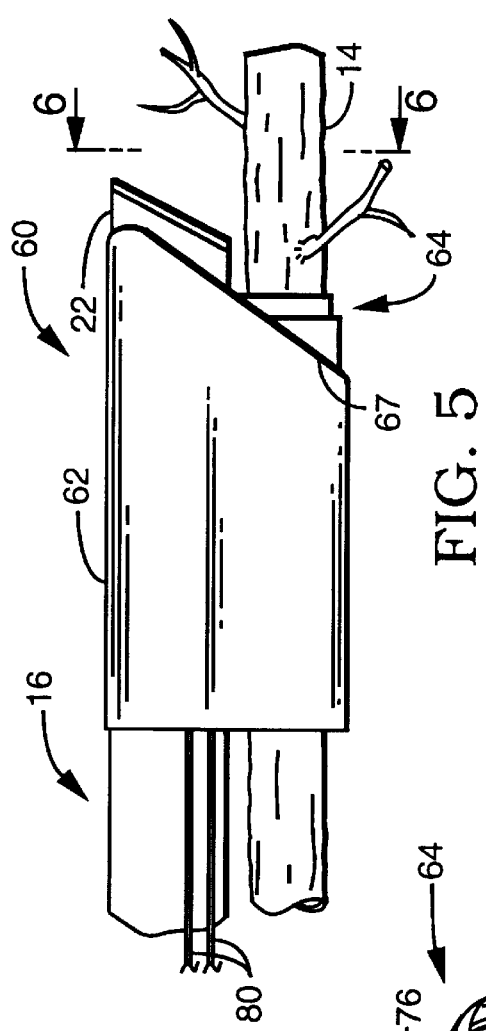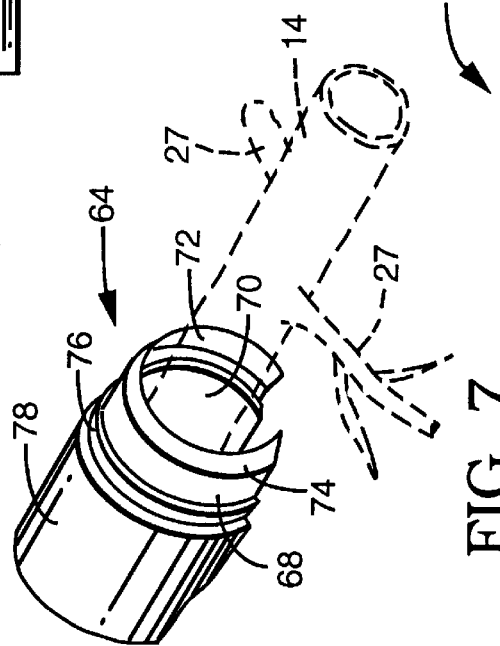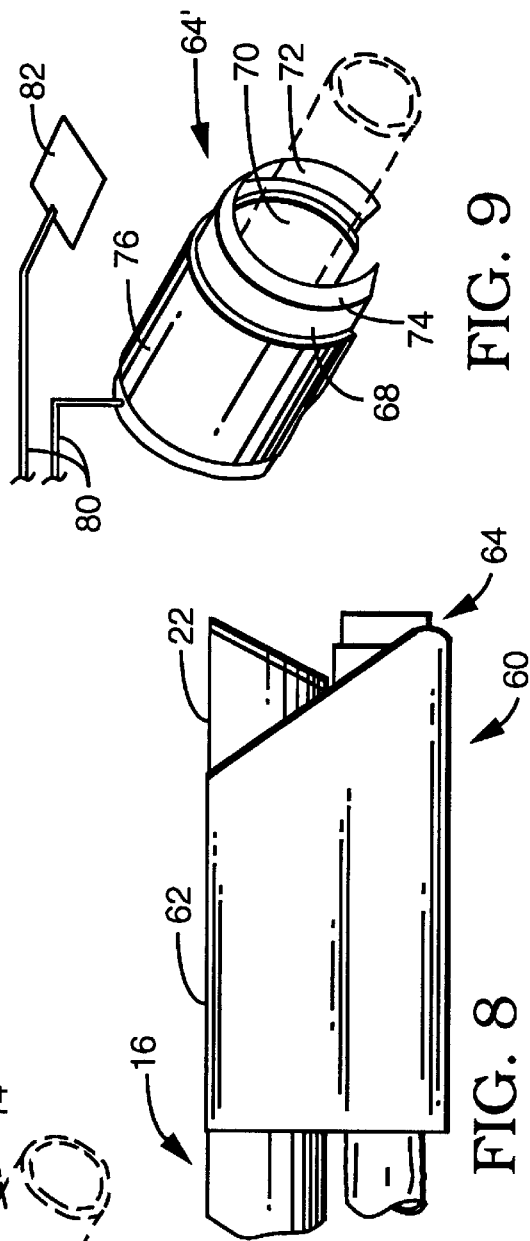

METHOD AND APPARATUS FOR THE MINIMALLY INVASIVE HARVESTING OF A SAPHENOUS VEIN AND THE LIKE

BACKGROUND OF THE INVENTION

The present invention relates to surgical procedures for providing autografts for use in coronary artery bypass surgery and, in particular, to a procedure for the minimally invasive harvesting of veins such as the saphenous vein for use as a bypass autograft.

Vascular complications produced by atherosclerosis, such as stenosis, aneurysm, rupture or occlusion, in which the atherosclerosis disease is advanced and the health of a patient is jeopardized, call for surgical intervention. If the disease is extensive, the affected artery or other vessel is no longer reliable and usually is replaced or bypassed by a bypass graft, usually referred to as an "autograft." To this end, the involved section of the vessel is transected and ligated at a point distal to the stenosis, occlusion, etc., and a replacement graft is sutured to the vessel, as for example, by anastomosis surgery, to provide a bypass path for blood flow. In a patient who undergoes coronary artery bypass grafting (CABG) surgery, a non-critical artery or vein is harvested from elsewhere in the body and is sewn into place in such a manner that reestablishes the flow of blood to the heart region that had lost its supply of blood because of the atherosclerotic occlusion.

The saphenous vein in the leg is the vessel that is most commonly harvested for use as a bypass graft in coronary artery surgery. However, typical procedures for harvesting a saphenous vein autograft are tedious, time consuming, and cause undesirable patient trauma. In one harvesting procedure, an incision is made along the leg for a length corresponding to the length of the autograft required, wherein the vein is transected and is stripped from the leg. The incision then must be sutured or stapled along its length. In some patients, the incision must be made along the entire length of the leg. The surgery required for harvesting a graft in this manner is traumatic to the patient, increases recovery time, increases the patient's hospital confinement, and adds to the cost of the coronary artery surgery.

Accordingly, it would be highly desirable to provide a less invasive procedure for harvesting the saphenous vein for a CABG procedure which avoids the need for a long incision and subsequent stitching, while reducing the trauma and the recovery time experienced by the patient.

SUMMARY OF THE INVENTION

The present invention provides a minimally invasive procedure for harvesting a saphenous vein for use, for example, in coronary artery bypass grafting (CABG) procedures. This invention provides methods and apparatus requiring only a relatively small incision, generally at a distal location of the vein, and, in certain embodiments, a small stab incision at a proximal location of the vein where it is to be transected to provide the desired length or lengths of autograft.

By way of illustration, the invention includes a guide device or member of microsurgical dimensions which preferably is secured to, and provides a guide for, an endoscope which is used by a surgeon to view the saphenous vein as it is being harvested. In one embodiment, the guide member may be provided with an axial guiding slot, whereby the guide member has an opening traversing the guide member and allowing it to be pressed into engagement with the vein and with the guide slot concentrically aligned with the vein.

Thus, the guide member may be translated along with the attached endoscope externally along the vein under the patient's skin, with the saphenous vein itself providing guidance for the movement of the instrument. The guide member is also provided with integral means for supporting microsurgical cutting means such as surgical scissors, bipolar cutting device, etc., which is used by the surgeon to cut away from the vein all side branch vessels and tissues which are not separated by the guide member as it is advanced along the vein. The invention contemplates various configurations of the guide member, the integral supporting means as well as the cutting means itself. Thus, the guide member may include a plurality of lumens, single larger diameter lumen, or two smaller diameter lumens located at diametrically opposite sides of the saphenous vein, to allow access to the circumference of the vein by microsurgical scissors. In a one embodiment, a bipolar cutting means is configured to substantially provide the guiding slot and thus operates circumferentially about the saphenous vein which is loosely confined in the guide slot. The bipolar cutting means may include an electrically heated cutting blade which cuts away the side branch veins and other surrounding tissue and also cauterizes the incision as the vein is harvested.

The harvesting procedure of the present invention advantageously maintains the distal end of the endoscope, having the viewing lens, in substantially the same plane as the cutting means. By this method, the guide member provides the surgeon with an unobstructed view of the saphenous vein, the surrounding tissue, and the cutting means, thereby allowing the surgeon to precisely position and manipulate the cutting means during the harvesting procedure. In addition, the invention advantageously aids in the separation of the patient's surrounding tissues and skin from the saphenous vein as the instrument is advanced, which prevents the skin or tissues from blocking the viewing lens of the endoscope.

DESCRIPTION OF THE FIGURES

FIG. 1 is an embodiment of the invention having a microsurgical endoscope and scissors.

FIG. 2 is an embodiment of the invention having a plurality of lumens proximate to a guiding slot positioned at the vein.

FIG. 2A is one embodiment of the invention showing the orientation of a lumen, contains an endoscope, relative to the guide slot.

FIG. 3 is an alternative embodiment of the invention having an annular guide member with the cutting means and endoscope disposed therein.

FIG. 4 is an embodiment of the invention having a slanted face surface, an endoscope and cutting means associated therewith, and which does not require a discrete guide member in the distal end of the apparatus.

FIG. 5 is an embodiment of the invention having an electric cutting means operably associated with the guide slot.

FIG. 6 is a view along line 6—6 of FIG. 5 showing the positioning of the saphenous vein and the bipolar cutting means.

FIG. 7 is a bipolar cutting means of the invention which substantially surrounds a vein being harvested.

FIG. 8 is an embodiment of the invention having an endoscope traversing the guide member and a distal end of the endoscope proximate to a bipolar cutting device.

FIG. 9 is a monopolar cutting means of the invention which substantially surrounds a vein being harvested.

DESCRIPTION OF THE PREFERRED EMBODIMENTS

FIG. 1 is an embodiment 12 of the present invention used to harvest a vein such as a saphenous vein 14 in combination with microsurgical instruments and in particular with an endoscope 16 and surgical scissors 18. The embodiment 12 includes a guide member 20, informally termed a "sled", which is preferably formed from an electrically nonconductive biocompatible material such as a medical plastic. The guide member 20 may include a plurality of lumens for receiving surgical instruments such as the distal ends 22, 24 of an endoscope 16 and scissors 18 and may include a guide slot formed therein or affixed thereto as a fixture. The guide member 20 preferably includes at least one slanted surface 23 to present a streamlined configuration to the tissues surrounding the saphenous vein to minimize the resistance to the guide member 20 and trauma to the vein while also acting as a wedge for separating tissues and skin from the saphenous vein while the guide member 20 is advanced. The lumen or lumens for receiving the scissors may include extended tubes 25, 26 integrally formed with the guide member 20 of the same non-conductive, biocompatible material and of sufficiently large diameters to receive and support the distal end 24 and length 28 of other surgical apparatus such as scissors 18, which are used to snip small side vessels 27 and other surrounding tissues (not shown) away from the saphenous vein 14. The scissors 18 include an actuator 30 and are of conventional design. The endoscope 16 is generally conventional and includes a viewing lens at its distal end 22, which end may be steerable or disposed at a selected angle, and an eyepiece 32 for direct visualization of the saphenous vein 14 and the cutting means such as the scissors 18 during the harvesting procedure. The endoscope also may include a connector 34 for connection to a light source (not shown) to allow transmitting light to illuminate the surgical area if desired. Preferably, the endoscope 16 is modified to engage a receiving means of the guide member 20, as further described below.

FIGS. 2 is an embodiment 12 of the invention shown in the process of harvesting the saphenous vein 14. The guide member 20 preferably includes a lumen 35 dedicated to the endoscope 16 and having receiving means to secure and release the distal end 22 of the endoscope from a desired position relative to the guide member 20. To this end, FIG. 2A depicts a cross-section of the guide member 20, wherein the distal end 22 of the endoscope 16 is tapered to define a slight conical length which may be tightly forced into a matching tapered lumen 35 formed in the member 20 to operably define a receiving means. Alternatively, the receiving means may be defined by a demountable lock which may be provided by means of an O-ring 37 (shown in phantom line) concentrically mounted within the interior surface of the lumen 35, with the distal end 22 of the endoscope having an annular recess 39 about its circumference which mates with the O-ring 37 to releasably attach the guide member 20 to the endoscope 16.

In use, the invention is inserted through an incision, generally at a distal end of the saphenous vein in the leg (not shown) as in the procedure when performing a saphenectomy for removing varicose veins. Upon exposure of the vein and an initial transection of the tissues in the immediate region, the guide member 20 is axially aligned with the saphenous vein 14 and an axial guide slot 36 (shown partially in phantom line in FIG. 2) is pressed into loose engagement with the saphenous vein 14 as depicted. The attached endoscope 16 then may be used by the surgeon to gently urge the guide member 20 along the saphenous vein 14 to provide separation of the skin and tissues from the vein. The endoscope 16 permits viewing the tissues, the side branch vessels 27, and the end of the scissors 18, as the guide member 20 is advanced. The guide member 20 is provided with a plurality of lumens 38, 40 such that instruments such as surgical scissors can be manipulated adjacent to the vein. Preferably, the lumens 38, 40 are diametrically opposed relative to the confined vein 14, which allows the surgeon to slide the scissors 18 beyond the slanted face 23 of the guide member 20 to snip away tissues and side branch vessels 27 as depicted in FIG. 2. In the embodiment of FIG. 2, two lumens 38, 40 and an extended tube 25, 26 for each lumen 38, 40 preferably extends the length of the endoscope 16, which allows sliding the scissors 18 down one lumen 38 to transect tissues, and then withdrawing the scissors 18 from that lumen 38 and sliding it down the other lumen 40 to transect the tissues on the other side of the vein 14. Thus, a surgeon may access the full circumference of the saphenous vein via the lumens 38, 40, and by slight rotation of the guide member 20 if required.

FIG. 3 depicts an alternative embodiment 42, wherein a guide member 44 is comprised of an annular ring coaxially secured to a section of tube 46 via diametrically opposed spokes 48. The outer surface of the member 44 preferably is curved or beveled so as to present a streamlined outer surface 50 to the surrounding tissues during advancement of the guide member 44 along the saphenous vein 14. The inside surface of the tube 46 includes the endoscope lumen 35, modified as depicted in FIG. 2A to receive the distal end 22 of the endoscope 16. In this embodiment 42, specific guiding tubes and lumens for the scissors 18 are deleted. The scissors 18 may be slid along the length of the endoscope and through the annulus formed between the annular ring of member 44 at either side of the saphenous vein 14 to cut away the tissues, while the guide member 44 keeps skin and tissues away from the endoscope 16 to allow ready visualization of the procedure.

FIG. 4 depicts a further alternative embodiment 52, wherein a guide member 54 resembles the guide member 20 of FIG. 2 and includes the endoscope lumen 35, but does not include the additional integral lumens 38, 40 and extended tubes 25, 26. The embodiment includes the slanted face 23 to provide a streamlined guiding member 54 for separating tissues and skin from the saphenous vein 14, and includes the endoscope lumen 35 by which the distal end 22 of the endoscope 16 is fixed to the guide member 54 as previously described. In the embodiment of FIG. 4, the guide slot is dispensed with and a bottom surface 56 of the member 54 is employed by the surgeon to position the guide member 54 along the saphenous vein 14. The surgical scissors 18 likewise are guided into position at either side of the saphenous vein 14 by the guide member 54, and particularly by the bottom surface 56 thereof, to allow the surgeon to clip away surrounding tissue and side branch vessels 27. Rotation of the guide member 54 via the endoscope allows visualization of the entire exterior of the vein 14 so that all connected tissue may be removed. As in the other embodiments herein, the guide member 54 is used to separate surrounding tissue from the saphenous vein 14 while preventing the patient's skin from occluding the viewing lens of the endoscope and blocking the surgeon's view of the procedure.

FIGS. 5, 6 and 8 depict a further alternative embodiment 60 of the invention, wherein a guide member 62 is configured to accommodate an electrically energized monopolar or bipolar cutting device, generally designated at 64. The bipolar cutting device, depicted in greater detail in FIGS. 6 and 7, is generally cylindrical in configuration with an axially extending guide slot 66 formed therein to allow the guide member 62 to be pressed into engagement with the saphenous vein 14 as previously described in FIGS. 2 and 3.

As in FIGS. 1, 2, and 4, the guide member of FIG. 5 is provided with a slanted front 67 similar to face the slanted face 23 of previous description, but where the leading edge of the member 62 coincides with the endoscope lumen 35 at the distal end 22 of the endoscope 16, and slants back to the bipolar cutting device 64. This configuration provides added protection for the viewing lens of the endoscope 16.

Referring in particular to FIG. 7, the bipolar cutting device 64 comprises a sharpened cutting blade 68 of an electrically conductive metal, which is preferably circular and which is insulated from the saphenous vein confined therein by a layer of insulation 70 bonded to the inside cylindrical surface of the circular cutting blade 68. The end of the cutting blade 68 is comprised of a substantially circular cutting edge 72 and a beveled portion 74 to provide the capability to make a substantially circular incision proximate to and surrounding the saphenous vein 14. The cutting blade 68 is coated with a second layer of insulation 76 to insulate it from an electrically conductive current return electrode 78 disposed thereabout. An electrical current source (not shown) is coupled to the cutting blade 68 and to the return electrode 78 by means of insulated wires 80 (FIG. 5) extending the length of the endoscope 16, with the positive and negative terminals of the electrical source coupled to the cutting blade 68 and return electrode 78, respectively. As the guide member 62 is advanced along the saphenous vein 14, the bipolar cutting device 64 is energized when structures such as surrounding tissues or side branch vessels 27 are to be cut away. Electrical current flows through the cutting blade 68 and back to the return electrode 78, which heats the cutting blade 68 to temperatures which allow the cutting blade to cut through the tissues and side branch vessels while simultaneously cauterizing them to prevent bleeding.

The return electrode 78 may have alternate configurations while retaining the essential function as described herein. For example, the return electrode 78 may be a partial arc of metal insulated from, and disposed immediately above, the cutting blade 68. As depicted in FIG. 9, a monopolar cutting device 64' similar in configuration to the bipolar cutting device 64 shown in FIGS. 5–8 may be employed with the guide member 62. The return electrode 78 is not required and the return path for the electrical current is provided by attaching a negative electrode in the form of a patch 82 to the body of the patient. Insulated wires 80 supply electrical current to the cutting blade 68 and patch 82.

At such time as the guide member of the invention has been advanced a distance corresponding to the length of the autograft required for the subsequent CABG surgery, the saphenous vein may be transected as, for example, by a stab incision through the skin, and the end of the remaining vein may be ligated with a suture. Alternatively, the cutting scissors or bipolar device may be used to transect the vein where such action would be sufficiently hemostatic to stop any bleeding. The dissected saphenous vein 14 then may be simply pulled intact from its native location via the incision. As may be seen, the entire harvesting procedure is minimally invasive since only a small entry incision generally is necessary, while the extracted saphenous vein graft also experiences a minimum of trauma.

Although the invention is described herein relative to specific embodiments, various bipolar device may be used to transect the vein where such action would be sufficiently hemostatic to stop any bleeding. The dissected saphenous vein 14 then may be simply pulled intact from its native location via the incision. As may be seen, the entire harvesting procedure is minimally invasive since only a small entry incision generally is necessary, while the extracted saphenous vein graft also experiences a minimum of trauma.

Although the invention is described herein relative to specific embodiments, various additional features and advantages will be apparent from the description and drawings, and thus the scope of the invention is defined by the following claims and their equivalents.

What is claimed is:

1. Apparatus for harvesting a vein via a minimally invasive incision, including an endoscope and electrically energized tissue dissecting means, comprising:

a guide member for manipulation under the skin along the vein; an integral electrically energized cutting device comprised of a sharpened cutting blade and an electrically conductive metal;

a tubular endoscope lumen secured within said guide member for slideably supporting a distal end of the endoscope; and an axial guide slot coaxial to said endoscope lumen and formed within said guide member for receiving the vein and whereby said guide member may be advanced along the vein.

2. The apparatus of claim 1 wherein said electrically energized cutting device is circular and has a cylindrical layer of insulation.

3. The apparatus of claim 2 further comprising a second layer of insulation and a return electrode.

4. The apparatus of claim 1 wherein said guide member has a slanted front face.

* * * * *